United States Patent
Whitehurst et al.

(10) Patent No.: US 6,735,475 B1
(45) Date of Patent: May 11, 2004

(54) FULLY IMPLANTABLE MINIATURE NEUROSTIMULATOR FOR STIMULATION AS A THERAPY FOR HEADACHE AND/OR FACIAL PAIN

(75) Inventors: Todd K. Whitehurst, Sherman Oaks, CA (US); James P. McGivern, Stevenson Ranch, CA (US); Carla Mann Woods, Los Angeles, CA (US); Paul M. Meadows, Glendale, CA (US); Janusz A. Kuzma, Parker, CO (US)

(73) Assignee: Advanced Bionics Corporation, Sylmar, CA (US)

( * ) Notice: Subject to any disclaimer, the term of this patent is extended or adjusted under 35 U.S.C. 154(b) by 169 days.

(21) Appl. No.: 10/057,088

(22) Filed: Jan. 24, 2002

Related U.S. Application Data
(60) Provisional application No. 60/265,010, filed on Jan. 30, 2001.

(51) Int. Cl.[7] .................................................. A61N 1/30
(52) U.S. Cl. ......................................................... 607/46
(58) Field of Search ..................................... 607/1–114

(56) References Cited

U.S. PATENT DOCUMENTS

| | | |
|---|---|---|
| 4,537,195 A | 8/1985 | McDonnell |
| 5,193,539 A | 3/1993 | Schulman et al. |
| 5,193,540 A | 3/1993 | Schulman et al. |
| 5,215,086 A | 6/1993 | Terry, Jr. et al. |
| 5,312,439 A | 5/1994 | Loeb |
| 5,540,734 A | 7/1996 | Zabara |
| 5,569,166 A | 10/1996 | Stone |
| 6,016,449 A | 1/2000 | Fischell et al. |
| 6,051,017 A | 4/2000 | Loeb et al. |
| 6,132,392 A | 10/2000 | Stone |
| 6,161,044 A | 12/2000 | Silverstone |
| 6,185,452 B1 | 2/2001 | Schulman et al. |
| 6,208,902 B1 | 3/2001 | Boveja |
| 6,405,079 B1 | 6/2002 | Ansarinia |
| 6,464,687 B1 | 10/2002 | Ishikawa et al. |
| 6,505,075 B1 | 1/2003 | Weiner |
| 6,526,318 B1 | 2/2003 | Ansarinia |

FOREIGN PATENT DOCUMENTS

| | | |
|---|---|---|
| WO | WO-98/43700 A1 | 10/1998 |
| WO | WO-98/43701 A1 | 10/1998 |

OTHER PUBLICATIONS

Ahmed, et al., "Use of Percutaneous Electrical Nerve Stimulation (PENS) in the Short–Term Management of Headache", Headache, vol. 40(4), (Apr. 2000), pp. 311–315.

Anthony, M., "Cervicogenic Headache: Prevalence and Response t Local Steroid Therapy", Clin Exp Rheumatol, vol. 18(2 Suppl 19), (Apr. 2000), pp. S59–64.

Ben–Menachem, E., "Vagus Nerve Stimulation", Baillieres Clin Neurol, vol. 5(4), (Dec. 1996), pp. 841–848.

Biondi, DM., "Cervicogenic Headache: Mechanisms, Evaluation, and Treatment Strategies", J Am Osteopath Assoc, vol. 100(9 Suppl), (Sep. 200), pp. S7–14.

Cameron, et al., "Micromodular Implants to Provide Electrical Stimulation of Paralyzed Muscles and Limbs", IEEE Transactions on Biomedical Engineering, vol. 44, No. 9, (Sep. 1997), pp. 781–790.

(List continued on next page.)

*Primary Examiner*—Scott M. Getzow
(74) *Attorney, Agent, or Firm*—Laura Haburay Bishop

(57) ABSTRACT

A small implantable stimulator(s) with at least two electrodes is small enough to have the electrodes located adjacent to a nerve structure at least partially responsible for headache and/or facial pain. The small stimulator provides a means of stimulating a nerve structure(s) when desired, and may be implanted via a minimal surgical procedure.

19 Claims, 7 Drawing Sheets

OTHER PUBLICATIONS

Caputi, et al., "Therapeutic Blockade of Greater Occipital and Supraorbital Nerves in Migraine Patients", Headache, vol. 37(3), (Mar. 1997), pp. 174–179.

Farina, et al., "Headache and Cervical Spine Disorders: Classification and Treatment with Transcutaneous Electrical Nerve Stimulation", Headache, vol. 26(8), (Sep. 1986), pp. 432–433.

Hamel, E., "Current Concepts of Migraine Pathophysiology", Can J Clin Pharmacol, vol. 6 (Suppl. A), (1999 Autumn), pp. 9A–14A.

Hargreaves, et al., "Pathophysiology of Migraine—New Insights", Can J Neurol Sci, vol. 26(Suppl 3), (Nov. 1999), pp. S12–9.

Heydenreich, A., "Die Punktformige Transkutane Elektrische Nervenstimulation in der Migranetherapie [Punctate Transcutaneous Electrical Nerve Stimulation in Migraine Therapy]", Psychiatr Neurol Med Psychol (Leipz), vol. 40(12), (Dec. 1988), pp. 717–723.

May, et al., "The Trigeminovascular System in Humans: Pathophysiologic Implications for Primary Headache Syndromes of the Neural Influences on the Cerebral Circulation." J Cereb Blood Flow Metab, vol. 19(2), (Feb. 1999), pp. 115–127.

Pieper, et al., "Percutaneous Retrogasserian Glycerol Rhizolysis for Treatment of Chronic Intractable Cluster Headaches: Long–Term Results", Neurosurgery, vol. 46(2), (Feb. 2000), pp. 363–368; discussion pp. 368–370.

Salvesen, R., "Cluster headache", Curr Treat Options Neurol, vol. 1(5), (Nov. 1999), pp. 441–449.

Schreiber, et al., "Expression of Neuron–Specific Enolase in Adult Rat Brain Following Epilepticus", Exp Neurol, vol. 159(1), (Sep. 1999), pp. 329–331.

Solomon, et al., "Safety and Effectiveness of Cranial Electrotherapy in the Treatment of Tension Headache", Headache, vol. 29(7), pp. 445–450.

FULLY IMPLANTABLE MINIATURE NEUROSTIMULATOR FOR STIMULATION AS A THERAPY FOR HEADACHE AND/OR FACIAL PAIN

The present application claims the benefit of U.S. Provisional Patent Application Serial No. 60/265,010, filed Jan. 30, 2001, which application is incorporated herein by reference in its entirety.

FIELD OF THE INVENTION

The present invention generally relates to implantable stimulator systems and methods, and more particularly relates to implantable stimulator systems and methods utilizing one or more implantable microstimulators for treating headache and/or facial pain.

BACKGROUND OF THE INVENTION

The public health significance of headache and facial pain is often overlooked, probably because of their episodic nature and the lack of mortality attributed to them. Headache and facial pain disorders are, however, often incapacitating, with considerable impact on social activities and work, and may lead to significant consumption of drugs.

The International Headache Society (IHS) published "Classification and Diagnostic Criteria for Headache Disorders, Cranial Neuralgias and Facial Pain" in 1988. IHS identified 13 different general groupings of headache, given below in Table 1.1.

TABLE 1

Groupings of Headache Disorders and Facial Pain

1. Migraine
2. Tension-type headache
3. Cluster headache and chronic paroxysmal hemicrania
4. Miscellaneous headaches unassociated with structural lesions
5. Headache associated with head trauma
6. Headache associated with vascular disorders
7. Headache associated with non-vascular intracranial disorder
8. Headache associated with substances or their withdrawal
9. Headache associated with non-cephalic infections
10. Headaches associated with metabolic disorders
11. Headache or facial pain associated with disorder of cranium, neck, eyes, ears, nose, sinuses, teeth, mouth or other facial or cranial structures
12. Cranial neuralgias, nerve trunk pain and deafferentation pain
13. Non-classifiabie headache The IHS classification of the most common types of headache is summarized in Table 2, below.

TABLE 2

IHS Classification of Primary Headaches

1. Migraine
   1.1 Migraine without aura
   1.2 Migraine with aura
      1.2.1 Migraine with typical aura
      1.2.2 Migraine with prolonged aura
      1.2.3 Familial hemipiegic migraine headache
      1.2.4 Basilar migraine
      1.2.5 Migraine aura without headache
      1.2.6 Migraine with acute onset aura
   1.3 Ophthalmoplegic migraine
   1.4 Retinal migraine
   1.5 Childhood periodic syndromes that may be precursors to or associated with migraine
      1.5.1 Benign paroxysmal vertigo of childhood
      1.5.2 Alternating hemiplegia of childhood TABLE 2-continued IHS Classification of Primary Headaches 1.6 Complications of migraine
      1.6.1 Status migrainosus
      1.6.2 Migrainous infarction
   1.7 Migrainous disorder not fulfilling above criteria
2. Tension-type headache
   2.1 Episodic tension-type headache
      2.1.1 Episodic tension-type headache associated with disorder of pericranial muscles
      2.1.2 Episodic tension-type headache not associated with disorder of pericranial muscles
   2.2 Chronic tension-type headache
      2.2.1 Chronic tension-type headache associated with disorder of pericranial muscles
      2.2.2 Chronic tension-type headache not associated with disorder of pericranial muscles
   2.3 Headache of the tension-type not fulfilling above criteria
3. Cluster headache and chronic paroxysmal hemicrania
   3.1 Cluster Headache
      3.1.1 Cluster headache, periodicity undetermined
      3.1.2 Episodic cluster headache
      3.1.3. Chronic Cluster Headache
      3.1.3.1 Unremitting from onset
      3.1.3.2 Evolved from episodic
   3.2 Chronic paroxysmal hemicrania
   3.3 Cluster headache-like disorder not fulfilling above Criteria

Migraine Headache

The IHS classification provides diagnostic criteria for migraine without and with aura, summarized in Tables 3 and 4 below.

TABLE 3

IHS Diagnostic Criteria for Migraine Without Aura

A. At least five attacks fulfilling B-D
B. Headache attacks lasting 4–72 h (untreated or unsuccessfully treated)
C. Headache has at east two of the following characteristics:
   1.   Unilateral location
   2.   Pulsating quality
   3.   Moderate or severe intensity (inhibits or prohibits daily activities)
   4.   Aggravation by walking stairs or similar routine physical activity
D. During headache at least one of the following:
   1.   Nausea and/or vomiting
   2.   Photophobia and phonophobia
E. At least one of the following:
   1.   History and physical do not suggest headaches secondary to organic or systemic metabolic disease
   2.   History and/or physical and/or neurologic examinations do suggest such disorder, but is ruled out by appropriate investigations
   3.   Such disorder is present, but migraine attacks do not occur for the first time in close temporal relation to the disorder

TABLE 4

IHS Diagnostic Criteria for Migraine With Aura

A. At least two attacks fulfilling B
B. At least three of the following four characteristics:
   1.   One or more fully reversible aura symptoms indicating focal cerebral cortical and/or brain stem dysfunction
   2.   At least one aura symptom develops gradually over more than four minutes or two or more symptoms occur in succession
   3.   No aura symptom lasts more than 60 minutes. If more than one aura symptom is present, accepted duration is proportionally increased
   4.   Headache follows aura with a free interval of less than 60 minutes. It may also begin before or simultaneously with the aura.

TABLE 4-continued

IHS Diagnostic Criteria for Migraine With Aura

C. At least one of the following:
  1. History and physical and neurologic examinations do not suggest headaches secondary to organic or systemic metabolic disease
  2. History and/or physical and/or neurologic examinations do suggest such disorder, but it is ruled out by appropriate investigations
  3. Such disorder is present, but migraine attacks do not occur for the first time in close temporal relation to the disorder The IHS classification includes several different types of migraine variants. Basilar migraine is defined as a migraine with an aura involving the brainstem. Symptoms include ataxia, dysarthria, vertigo, tinnitus and/or changes in consciousness and cognition. Ophthalmoplegic migraine is associated with acute attacks of third nerve palsy with accompanying dilation of the pupil. In this setting, the differential diagnosis includes an intracranial aneurysm or chronic sinusitis complicated by a mucocele. The ophthalmoplegia can last from hours to months. Hemiplegic migraine is distinguished by the accompanying hemiplegia, which can be part of the aura, or the headache may precede the onset of hemiplegia. Hemiplegic migraine can be familial and may last for days or weeks, clinically simulating a stroke. An additional differential diagnosis includes focal seizures.

Status migrainosus describes a migraine lasting longer than 72 hours with intractable debilitating pain, and typically occurs in a setting of inappropriate and prolonged use of abortive anti-migraine drugs. These patients may require hospitalization, both for pain control, detoxification from the abused drugs, and treatment of dehydration resulting from prolonged nausea and vomiting.

A migraine prevalence survey of American households was conducted in 1992, and included 20,468 respondents 12–80 years of age. Using a self-administered questionnaire based on modified IHS criteria; 17.6% of females and 5.7% of males were found to have one or more migraine headaches per year. A projection to the total US population suggests that 8.7 million females and 2.6 million males suffer from migraine headache with moderate to severe disability. Of these, 3.4 million females and 1.1 million males experience one or more attacks per month. Prevalence is highest between the ages of 25 and 55, during the peak productive years.

Based on published data, the Baltimore County Migraine Study, MEDSTAT's MarketScan medical claims data set, and statistics from the Census Bureau and the Bureau of Labor Statistics, it has been estimated that migraineurs require 3.8 bed rest days for men and 5.6 days for women each year, resulting in a total of 112 million bedridden days. Migraine costs American employers about $13 billion a year because of missed workdays and impaired work function; close to $8 billion is directly due to missed workdays. Patients of both sexes aged 30 to 49 years incurred higher indirect costs compared with younger or older employed patients. Annual direct medical costs for migraine care are about $1 billion, with about $100 spent per diagnosed patient. Physician office visits account for about 60% of all costs; in contrast, emergency department visits contribute less than 1% of the direct costs.

Tension-Type Headache

The diagnostic criteria for tension-type headaches are summarized in Table 5, below. However, migraine symptoms may overlap considerably with that of tension-type headaches. Tension-type headaches are believed by some experts to be a mild variant of migraine headache. Patients with tension-type headaches who also have migraines may experience nausea and vomiting with a tension headache, though when they do, it typically is mild and for a shorter duration compared to that with a migraine. Tension-type headache may be a disorder unto itself in individuals who do not have migraines, and may manifest as attacks of mild migraine in individuals with migraines.

TABLE 5

IHS Criteria for Various Forms of Tension-Type Headache

Tension-type headache

At least two of the following pain characteristics:
  1. Pressing/tightening (non-pulsating) quality
  2. Mild or moderate intensity (may inhibit, but does not prohibit activities)
  3. Bilateral location
  4. No aggravation by walking stairs or similar routine physical activity
Both of the following:
  1. No nausea or vomiting (anorexia may occur)
  2. Photophobia and phonophobia absent, or only one is present
At least one of the following:
  1. History and physical do not suggest headaches secondary to organic or systemic metabolic disease
  2. History and/or physical and/or neurologic examinations do suggest such disorder, but is ruled out by appropriate investigations
  3. Such disorder is present, but tension-type headache does not occur for the first time in close temporal relation to the disorder Episodic tension-type headache (ETTH)

Diagnostic criteria:
  A. At least 10 previous episodes, <180 days/year (<15/mo) with headache
  B. Headache lasting from 30 minutes to 7 days Chronic tension-type headache (CTTH)

Diagnostic criteria:
  A. Average frequency ≧1 day/month (≧189 days/year) for ≧6 months Tension-type headache associated with disorder of pericranial muscles At least one of the following:
  1. Increased tenderness of pericranial muscles demonstrated by manual palpation or pressure algometer.
  2. Increased electromyographic level of pericranial muscles at rest or during physiologic tests.

Tension-type headache not associated with pericranial muscle disorder

No increased tenderness of pericranial muscles. If studied, electromyography of pericranial muscles shows normal levels of activity.

Based on a telephone survey of 13,345 people, the 1-year period prevalence of episodic tension-type headache (ETTH) is estimated to be 38.3%, according to IHS criteria. Women had a higher 1-year ETTH prevalence than men in all age, race, and education groups, with an overall prevalence ratio of 1.16. Prevalence peaked in the 30- to 39-year-old age group in both men (42.3%) and women (46.9%). Prevalence increased with increasing educational levels in both sexes, reaching a peak in subjects with graduate school educations of 48.5% for men and 48.9% for women. Of subjects with ETTH, 8.3% reported lost workdays because of their headaches, while 43.6% reported decreased effectiveness at work, home, or school.

Chronic Daily Headache

Chronic tension-type headache (CTTH) is a subtype of tension headaches, with patients experiencing headaches daily or almost every day. In practice, the term "chronic daily headache" is commonly used to describe headaches lasting for greater than 4 hours per day and for at least 15 days per month. The classification of chronic daily headaches is summarized below in Table 6.

TABLE 6

Classification of Chronic Daily Headache

Transformed migraine

1. With medication overuse
    2. Without medication overuse

Chronic tension-type headache (CTTH)

1. With medication overuse
    2. Without medication overuse

New daily persistent headache

1. With medication overuse
    2. Without medication overuse

Hemicrania continua

1. With medication overuse
    2. Without medication overuse

In the study of 13,345 people cited above, the 1-year period prevalence of chronic tension-type headache (CTTH) was estimated to be 2.2%. This prevalence was higher in women and declined with increasing education. Subjects with CTTH reported more lost workdays (mean of 27.4 days vs. 8.9 days for those reporting lost workdays) and reduced-effectiveness days (mean of 20.4 vs. 5.0 days for those reporting reduced effectiveness) compared with subjects with ETTH.

Chronic daily headaches are best conceptualized as an umbrella category term, referring to a group of headache disorders characterized by headaches which occur greater than 15 days per month, with an average untreated duration of greater than 4 hours per day. There are many secondary causes of chronic daily headache, including post-traumatic headache, arteritis, intracranial mass lesions, etc. There are also short-lived primary headache disorders that occur greater than 15 days per month, such as chronic cluster headache or the paroxysmal hemicranias. These secondary and short-lived disorders are outside the scope of this discussion. The most common primary, chronic daily headache disorders include transformed migraine, chronic tension-type headaches, new daily persistent headache, or hemicrania continua. Each of these diagnoses can be complicated by medication overuse (e.g., barbiturates, acetaminophen, aspirin, caffeine, ergotamine tartrate and opioids). When used daily, all of these medications can lead to a vicious cycle of rebound headaches.

Cluster Headache

The 1988 IHS classification system recognized the uniqueness of cluster headache as a clinical and epidemiological entity. Formerly classified as a vascular migraine variant, cluster headache (a.k.a. suicide headache) is thought to be one of the most severe headache syndromes. It is characterized by attacks of severe pain, generally unilateral and orbital and lasting 15 minutes to 3 hours, with one or more symptoms such as unilateral rhinorrhea, nasal congestion, lacrimation, and conjunctival injection. In most patients, headaches occur in episodes, generally with a regular time pattern. These "cluster periods" last for weeks to months, separated by periods of remission lasting months to years. It primarily affects men, and in many cases, patients have distinguishing facial, body, and psychological features. Several factors may precipitate cluster headaches, including histamine, nitroglycerin, alcohol, transition from rapid eye movement (REM) to non-REM sleep, circadian periodicity, environmental alterations, and change in the level of physical, emotional, or mental activity. The IHS classification system gives specific diagnostic criteria for cluster headache, as given in Table 7 below.

TABLE 7

IHS Diagnostic Criteria for Cluster Headache 3.1 Cluster Headache
A. At least 5 attacks fulfilling B–D
B. Severe unilateral, orbital, supraorbital and/or temporal pain
    lasting 15–180 minutes untreated
C. At least one of the following signs present on the pain side:
    1. Conjunctival injection
    2. Lacrimation
    3. Nasal congestion
    4. Rhinorrhea
    5. Forehead and facial sweating
    6. Miosis
    7. Ptosis
    8. Eyelid edema
D. Frequency of attacks: from 1 every other day to 8 per day
E. At least one of the following:
    1. History, physical and neurological examinations do not suggest
        one of the disorders listed in groups 5–11 of Table 1
    2. History and/or physical and/or neurological examinations do
        suggest such disorder, but it is ruled out by appropriate
        investigations
    3. Such disorder is present, but cluster headache does not occur
        for the first time in close temporal relation to the disorder
3.1.1 Cluster headache periodicity undefined
    A. Criteria for 3.1 fulfilled
    B. Too early to classify as 3.1.2 or 3.1.3
3.1.2 Episodic cluster headache
Description: Attacks lasting between 1 week and 3 months occur in periods lasting 1 week to one year separated by pain free periods lasting 14 days or more.
    A. All the letter headings of 3.1
    B. At least 2 periods of headaches (cluster periods) lasting
        (untreated) from 7 days to one year, separated by remissions
        of at least 14 days.
3.1.3 Chronic cluster headache
Description: Attacks lasting between 2 weeks and 3 months occur for more than one year without remission or with remissions lasting less than 14 days.
    A. All the letter headings of 3.1
    B. Absence of remission phases for one year or more or with
        remissions lasting less than 14 days.
3.1.3.1 Chronic cluster headache unremitting from onset
    A. All the letter headings of 3.1.3
    B. Absence of remission periods lasting 14 days or more from
        onset.
3.1.3.2 Chronic cluster headache evolved from episodic
    A. All the letter headings of 3.1.3
    B. At least one interim remission period lasting 14 days or more
        within one year after onset, followed by unremitting course
        for at least one year.

The estimated prevalence of cluster headache is 69 cases per 100,000 people. Men are affected more commonly than women in a proportion of 6:1. Although most patients begin experiencing headache between the ages of 20 and 50 years (mean of 30 years), the syndrome may begin as early as the first decade and as late as the eighth decade.

Cervicogenic Headache

Cervicogenic headache (CEH) is a headache with its origin in the neck area. The source of pain is in structures around the neck that have been damaged. These structures can include joints, ligaments, muscles, and cervical discs, all of which have complex nerve endings. When these structures are damaged, the nerve endings send pain signals up the pathway from the upper nerves of the neck to the brainstem. These nerve fibers may synapse in the same brainstem nuclei as the nerve fibers of the trigeminal nerve. Since the trigeminal nerve is responsible for the perception of head pain, the patient experiences the symptoms of headache and/or facial pain.

While many patients who are diagnosed with CEH have the traditional symptoms of tension-type headache, some of the patients who have the traditional symptoms of migraine and cluster headache also respond to CEH diagnosis and treatment.

Facial Pain

Facial pain may be due to a number of underlying disorders. Among the most common is Trigeminal Neuralgia (also known as tic douloureux). More than 50,000 people in the US suffer from trigeminal neuralgia. It is a disorder of the trigeminal nerve that causes episodes of intense, stabbing, electric shock-like pain in the areas of the face where the branches of the nerve are distributed—lips, eyes, nose, scalp, forehead, upper jaw, and lower jaw. A less common form of the disorder, Atypical Trigeminal Neuralgia, may cause less intense, constant, dull burning or aching pain, sometimes with occasional electric shock-like stabs. Both forms of the disorder most often affect one side of the face, but some patients experience pain at different times on both sides. Onset of symptoms occurs most often after age 50, and it affects women more often than men. For patients with this disorder, an ordinary touch of the face, such as when brushing teeth or applying makeup, can trigger an attack. Trigeminal neuralgia is believed to be due to hyper-excitability of fibers of the trigeminal nerve or its ganglion. Microelectrode recordings from the trigeminal ganglion have demonstrated sustained high-frequency bursts during pain episodes of trigeminal neuralgia.

Trigeminal neuralgia may be treated medically with drugs that decrease neural excitability, e.g., carbamazepine or phenytoin. Such medications prove ineffective for many patients over the course of the disease. Thus, a number of surgical interventions (e.g., microvascular decompression of the trigeminal ganglion or it nerve fibers, radio-frequency rhizotomy) have been developed.

Another cause of facial pain is Temporomandibular Joint (TMJ) Dysfunction Syndrome. Most TMJ discomfort is temporary and can be treated with inexpensive remedies. However, some TMJ dysfunction patients are afflicted with persistent and sometimes unbearable pain. The symptoms of this chronic dysfunction include persistent pain in the facial muscles on one or both sides, a clicking or popping sensation when opening the mouth or working the jaw, recurring headaches, and difficulty chewing. Analgesics and anti-inflammatory medication may relieve the pain in some patients, and others turn to TMJ surgery in desperation.

Yet another cause of facial pain is Postherpetic Neuralgia, which is a possible complication of herpes zoster reactivation ("Shingles"). Shingles is a painful disease caused by reactivation of the herpes zoster virus (which causes chicken pox upon initial infection). It can affect the torso or limbs (spinal ganglia shingles) or the face (trigeminal ganglia shingles). Approximately one in five adults develops shingles, usually after age 50. For most people, shingles is an acute condition with pain typically lasting one month. However, in older patients or patients with a compromised immune system, postherpetic neuralgia, a very painful chronic condition, may develop. The incidence of postherpetic neuralgia is almost negligible before age 50, but at least 50% of patients older than 60 years and almost 75% beyond age 70 become affected following a shingles attack. Postherpetic neuralgia tends to improve over time without treatment. Some estimates suggest that only 2%–3% of patients have pain lasting more than one year. However, since more than 60,000 new cases develop annually in the US, the collective morbidity is still substantial. Treatment of postherpetic neuralgia consists of symptomatic relief of severe pain with tricyclic antidepressants and opioids.

BRIEF SUMMARY OF THE INVENTION

The invention disclosed and claimed herein provides means for chronically stimulating a trigeminal ganglion or ganglia, a trigeminal nerve(s), or branch(es) of a trigeminal nerve(s) with a miniature implantable neurostimulator that can be implanted with a minimal surgical procedure. This invention also provides means for chronically stimulating any nerve(s) arising from the upper cervical spine (i.e., C1–C4), including a greater occipital nerve(s), a lesser occipital nerve(s), a third occipital nerve(s), a great auricular nerve(s), a transverse cervical nerve(s), a supraclavicular nerve(s), or a branch(es) of any of these neural structures with a miniature implantable neurostimulator that can be implanted with a minimal surgical procedure. Electrical stimulation of such targets may provide significant therapeutic benefit in the management of migraine, tension-type headache, cluster headache, cervicogenic headache, other types of headache, and/or facial pain.

To treat migraine, tension-type headache, cluster headache, cervicogenic headache, other types of headache, and/or facial pain, a miniature implantable neurostimulator, such as a Bionic Neuron (also referred to as a BION™ microstimulator) may be implanted via a minimal surgical procedure (e.g., injection or small incision) adjacent to a trigeminal ganglion or ganglia, a trigeminal nerve(s), a branch(es) of a trigeminal nerve(s) (e.g., an ophthalmic nerve(s), a maxillary nerve(s), and/or a mandibular nerve (s)), or a branch(es) of any of these neural structures. A BION may additionally or alternatively be implanted adjacent to any nerve(s) arising from the upper cervical spine (i.e., C1–C4), including a greater occipital nerve(s), a lesser occipital nerve(s), a third occipital nerve(s), a great auricular nerve(s), a transverse cervical nerve(s), a supraclavicular nerve(s), or a branch(es) of any of these neural structures to treat migraine, tension-type headache, cluster headache, cervicogenic headache, other types of headache, and facial pain.

A microstimulator may be implanted via injection and/or via endoscopic means. A more complicated surgical procedure may be required for sufficient access to a particular nerve (e.g., a nerve surrounded by scar tissue) or for purposes of fixing the neurostimulator in place. A single microstimulator may be implanted, or two or more microstimulators may be implanted to achieve greater stimulation of one or more nerves.

The microstimulator used with the present invention possesses one or more of the following properties, among others:
  at least two electrodes for applying stimulating current to surrounding tissue;
  electronic and/or mechanical components encapsulated in a hermetic package made from biocompatible material(s);
  an electrical coil or other means of receiving energy and/or information inside the package, which receives power and/or data by inductive or radio-frequency (RF)

coupling to a transmitting coil placed outside the body, thus avoiding the need for electrical leads to connect devices to a central implanted or external controller;

means for receiving and/or transmitting signals via telemetry;

means for receiving and/or storing electrical power within the microstimulator; and a form factor making the microstimulator implantable via a minimal surgical procedure.

A microstimulator may operate independently, or in a coordinated manner with other implanted devices, or with external devices. For instance, a microstimulator may incorporate means for sensing a patient's condition, which it may then use to control stimulation parameters in a closed loop manner. The sensing and stimulating means may be incorporated into a single microstimulator, or a sensing means may communicate sensed information to at least one microstimulator with stimulating means.

BRIEF DESCRIPTION OF THE DRAWINGS

The above and other aspects of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

Figure 1A:
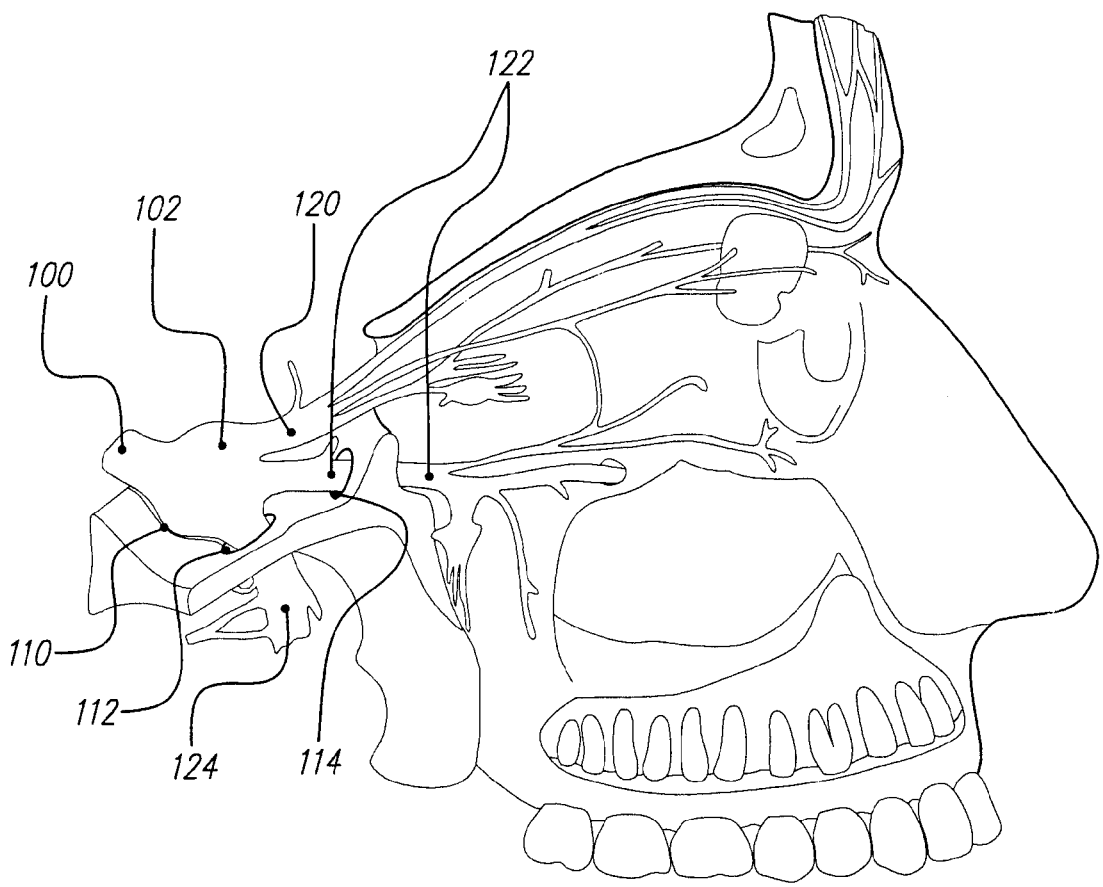
FIG. 1A depicts various nerve branches dorsal to the trigeminal nerve and nearby bony structures.

The following description is of the best mode presently contemplated for carrying out the invention. This description is not to be taken in a limiting sense, but is made merely for the purpose of describing the general principles of the invention. The scope of the invention should be determined with reference to the claims.

The mechanism of migraine is not well understood. Prevalent theories suggest that it is a central nervous system neurovascular disorder and that the trigeminal nerve may play a prominent role. The trigeminal nerve carries virtually all of the sensation from the face, and thus it likely plays a role in any pain that is referred to the front or the top of the head.

In "Pathophysiology of migraine—new insights" (Canadian Journal of neurological sciences, 1999 November), Hargreaves, et al. state that "The exact nature of the central dysfunction that is produced in migraineurs is still not clear and may involve spreading depression-like phenomena and activation of brainstem monoaminergic nuclei that are part of the central autonomic, vascular, and pain control centers. It is generally thought that local vasodilation of intracranial extracerebral blood vessels and a consequent stimulation of surrounding trigeminal sensory nervous pain pathways is a key mechanism underlying the generation of headache pain associated with migraine. This activation of the 'trigeminovascular system' is thought to cause the release of vasoactive sensory neuropeptides, especially CGRP, that increase the pain response. The activated trigeminal nerves convey nociceptive information to central neurons in the brain stem trigeminal sensory nuclei that in turn relay the pain signals to higher centers where headache pain is perceived. It has been hypothesized that these central neurons may become sensitized as a migraine attack progresses." The disorder of migraine may ultimately evoke changes in blood vessels within pain-producing intracranial meningeal structures that give rise to headache pain.

Hargreaves, et al. further state that "The 'triptan' antimigraine agents (e.g., sumatriptan, rizatriptan, zolmitriptan, and naratriptan) are serotonergic agonists that have been shown to act selectively by causing vasoconstriction through 5-HT1B receptors that are expressed in human intracranial arteries and by inhibiting nociceptive transmission through an action at 5-HT1D receptors on peripheral trigeminal sensory nerve terminals in the meninges and central terminals in brainstem sensory nuclei. These three complementary sites of action underlie the clinical effectiveness of the 5-HT1B/1D agonists against migraine headache pain and its associated symptoms."

In "Current concepts of migraine pathophysiology" (Canadian Journal of neurological sciences, 1999 Autumn), Hamel cites evidence that indicates migraine originates in the brain and, in its process and evolution, affects the meningeal blood vessels and leads to the development of head pain. Hamel states that: "This manifestation is related to the activation of the trigeminovascular sensory nerves, which release neuropeptides that mediate vasodilation, and the proinflammatory reaction thought to be involved in pain generation and transmission. Such a concept underscores the fact that the relationship between the nerves and the blood vessels is of paramount importance in the manifestation of the disease's symptoms."

It has also been suggested that primary headache syndromes, such as cluster headache and migraine, share an anatomical and physiologic substrate, namely the neural innervation of the cranial circulation. In "The trigeminovascular system in humans: pathophysiologic implications for primary headache syndromes of the neural influences on the cerebral circulation" (Journal of Cerebral Blood Flow Metabolism, 1999 February), May, et al. report that observation of vasodilation were made in an experimental trigeminal pain study, and conclude that the observed dilation of these vessels in trigeminal pain is not inherent to a specific headache syndrome, but rather is a feature of the trigeminal neural innervation of the cranial circulation. May, et al. also state that clinical and animal data suggest that the observed vasodilation is, in part, an effect of a trigeminoparasympathetic reflex. They suggest that the trigeminal innervation of the cranial circulation, and the observed vasodilation of the associated vasculature during headache syndromes, may be an underlying pathophysiological mechanism of headache.

In "Cluster headache" (Current Treatment Options in Neurology, 1999 November), Salvesen suggests a possible link between the trigeminal nerve and cluster headache when he states that: "For a very limited group of patients with chronic cluster headache, surgery may be a last resort.

The best surgical options are probably radio-frequency rhizotomy or microvascular decompression of the trigeminal nerve."

A study of long-term results with percutaneous retrogasserian glycerol rhizolysis for treatment of chronic intractable cluster headaches in 18 patients, fifteen patients (83%) obtained immediate pain relief after one or two injections; the majority of them experienced relief after the first injection. However, cluster headache recurred in seven patients (39%) over the course of the study, suggesting that permanent trigeminal destruction may not be an effective treatment.

The trigeminocervical nucleus is a region of the upper cervical spinal cord where sensory nerve fibers in the descending tract of the trigeminal nerve converge with sensory fibers from the upper cervical roots, e.g., the greater and lesser occipital nerves. This convergence of nociceptive pathways allows for the referral of pain signals from the neck to the trigeminal sensory receptive fields of the face and head as well as activation of the trigeminovascular neuroinflammatory cascade, which is generally believed to be one of the important pathophysiologic mechanisms of migraine. Also relevant to this condition is the convergence of sensorimotor fibers of the spinal accessory nerve and upper cervical nerve roots, which ultimately converge with the descending tract of the trigeminal nerve.

Cervicogenic headache is a chronic, hemicranial pain syndrome in which the sensation of pain originates in the cervical spine or soft tissues of the neck and is referred to the head. A study of 180 patients with CEH attempted to achieve headache relief blockade of the greater and lesser occipital nerves in the upper neck, on the side habitually affected by the headache. The patients were predominantly female, with a frequency of 18 headaches monthly. Injections of the long-acting corticosteroid depot methylprednisolone into the region of the greater and lesser occipital nerves produced complete relief of headache in 169 out of 180 patients with CEH for a period ranging from 10 to 77 days, the mean duration of relief being 23.5 days. However, similar relief of headache could be achieved in patients with attacks of strictly unilateral migraine or cluster headache, suggesting that local steroid injections by blocking the cervicotrigeminal relay, can arrest other forms of unilateral headache.

A study of 27 patients with migraine unresponsive to several combinations of pharmacological treatments, investigated the therapeutic value of greater occipital and trigeminal (i.e., supraorbital) nerve blockade. Patients were given repeated anesthetic blocks, on alternate days, up to a maximum of 10 blocks. Perineural injections of 0.5 to 1.0 mL of 0.5% bupivacaine, a local anesthetic were given at the epicranial emergence points of the above nerves in relation to the distribution of the cephalic pain only if such nerves were conspicuously pain sensitive to pressure. Clinical evaluation was determined by a monthly Total Pain Index and recording of the number of migraine attacks and analgesic consumption each month. A patient was considered responsive when the Total Pain Index decreased by 50% or more in the first month after treatment. 23 patients (85%) responded beneficially and maintained a favorable response for the 6-month period of observation. The treatment was considered to be of long-lasting effectiveness and without any side effects. 4 patients (15%) were unresponsive to treatment. The authors hypothesize that the anesthetic blocks extinguished presumed foci of nociceptor discharges maintained by perivascular neurogenic inflammation, thereby reestablishing normal central neuron sensitivity.

For many years, Transcutaneous Electrical Nerve Stimulation (TENS) has been applied with some success to the control of headache and facial pain symptoms. TENS is used to modulate the stimulus transmissions by which pain is felt by applying low-voltage electrical stimulation to large peripheral nerve fibers via electrodes placed on the skin. A study of 282 migraineurs had patients undergo Punctual (i.e., episodic) Transcutaneous Electrical Nerve Stimulation (PuTENS) via pocket electrostimulators. After more than 6 months PuTENS was prophylactically effective in 225 patients (80%), i.e., their frequency of attacks and use of drugs were reduced at least 50%. In the 90 patients treated by a physician, the rate of improvement was 86%, compared to 76% in 192 patients who self-administered the treatment according to a physician's instruction and under medical supervision. Applying the pocket electrostimulator at home, 96 out of 160 patients with migraine could alleviate their acute headache.

Other devices require that a needle electrode(s) be inserted through the skin during stimulation sessions. A study of 30 patients with tension headache, migraine, or posttraumatic headache symptoms of at least 6 months' duration evaluated the short-term effects of percutaneous electrical nerve stimulation (PENS). All treatments were administered for 30 minutes, three times a week for two consecutive weeks with one week off between the two different treatments. An alternating electrical stimulation frequency of 15 and 30 Hz was used. A "needle-only" control group was included. Pain, activity, and sleep scores were assessed using a 10-cm visual analog scale, with 0 corresponding to the best and 10 to the worst, during the 48-hour period prior to the beginning of the two treatments, immediately before and after each treatment session, and 48 hours after completing each treatment modality. Compared with the needles alone, PENS therapy was significantly more effective in decreasing the overall Visual Analog Scores (VAS) of pain for tension-type headache, migraine and posttraumatic headache (58%, 59%, and 52% versus 20%, 15%, and 20%, respectively). Similarly, PENS therapy produced greater improvement in the patients' physical activity (41% to 58% for PENS versus 11% to 21% for needles only) and quality of sleep (41% to 48% for PENS versus 12% to 20% for needles only).

In addition, Advanced Neuromodulation Systems (ANS) of Plano, Tex. has gained FDA approval to launch a pilot clinical study of its Genesis Totally Implantable Pulse Generator (IPG) Spinal Cord Stimulator (SCS) for relief of chronic severe headaches. This will presumably work by stimulating the upper cervical spinal cord in those patients with cervicogenic headaches. Surgically implanted stimulators, such as SCS systems, have been described in the art. These stimulators have different forms, but are usually comprised of an implantable control module (i.e., IPG) to which is connected to a series of leads that must be routed to nerve bundles in the spinal cord, to nerve roots and/or spinal nerves emanating from the spinal cord, or to peripheral nerves. The implantable devices are relatively large and expensive. In addition, they require significant surgical procedures for placement of electrodes, leads, and IPG. These devices may also require an external apparatus that needs to be strapped or otherwise affixed to the skin. Drawbacks, such as size (of internal and/or external components), discomfort, inconvenience, complex surgical procedures, and/or only acute or intermittent use has generally confined their use to patients with severe symptoms and the capacity to finance the surgery.

Recently, an alternative to 1) TENS, 2) percutaneous stimulation, and 3) bulky implantable stimulation assemblies has been introduced. Small, implantable microstimulators can be injected into soft tissues through a cannula or needle. See, e.g., U.S. Pat. Nos. 5,324,316 and 5,405,367, both of which patents are incorporated herein by reference. Discussed herein are ways to effectively use such small, fully implantable, chronic neurostimulators for treating headache and facial pain.

Figure 1B:
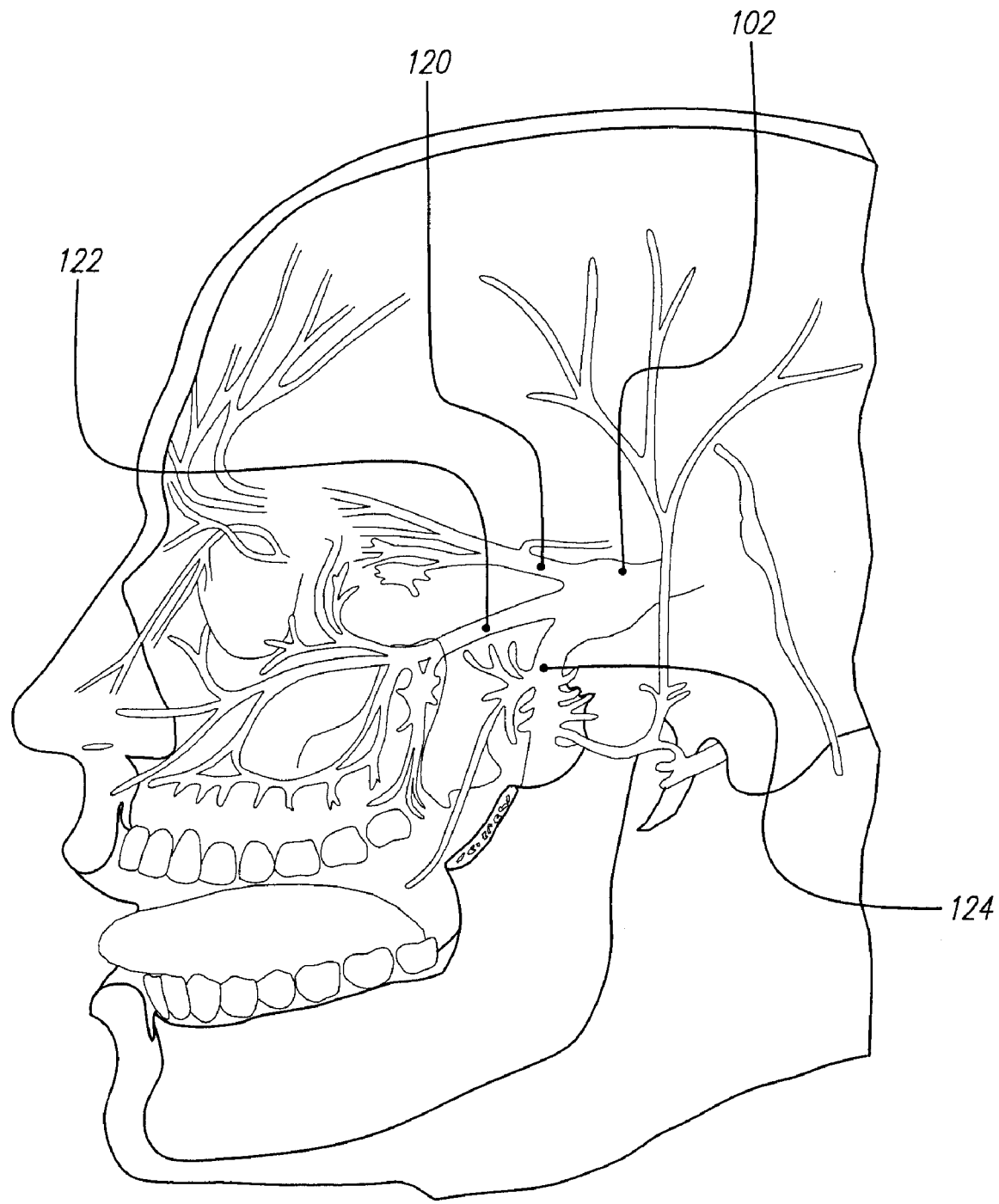
FIG. 1B illustrates the trigeminal nerve, and nerve branches dorsal and proximal to the trigeminal nerve.
Figure 2A:
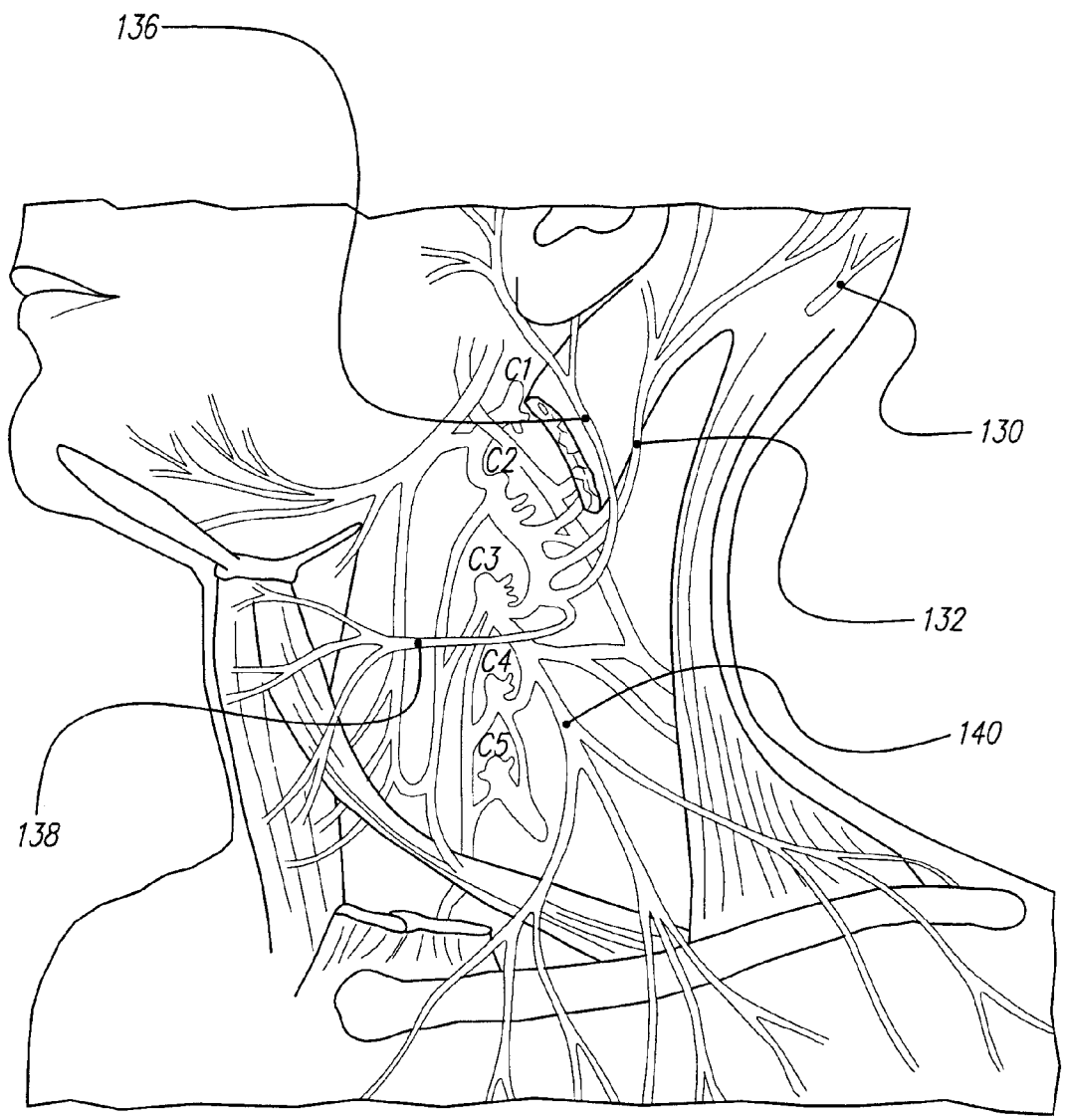
FIG. 2A illustrates the cervical plexus, depicting various nerves and muscles.
Figure 2B:
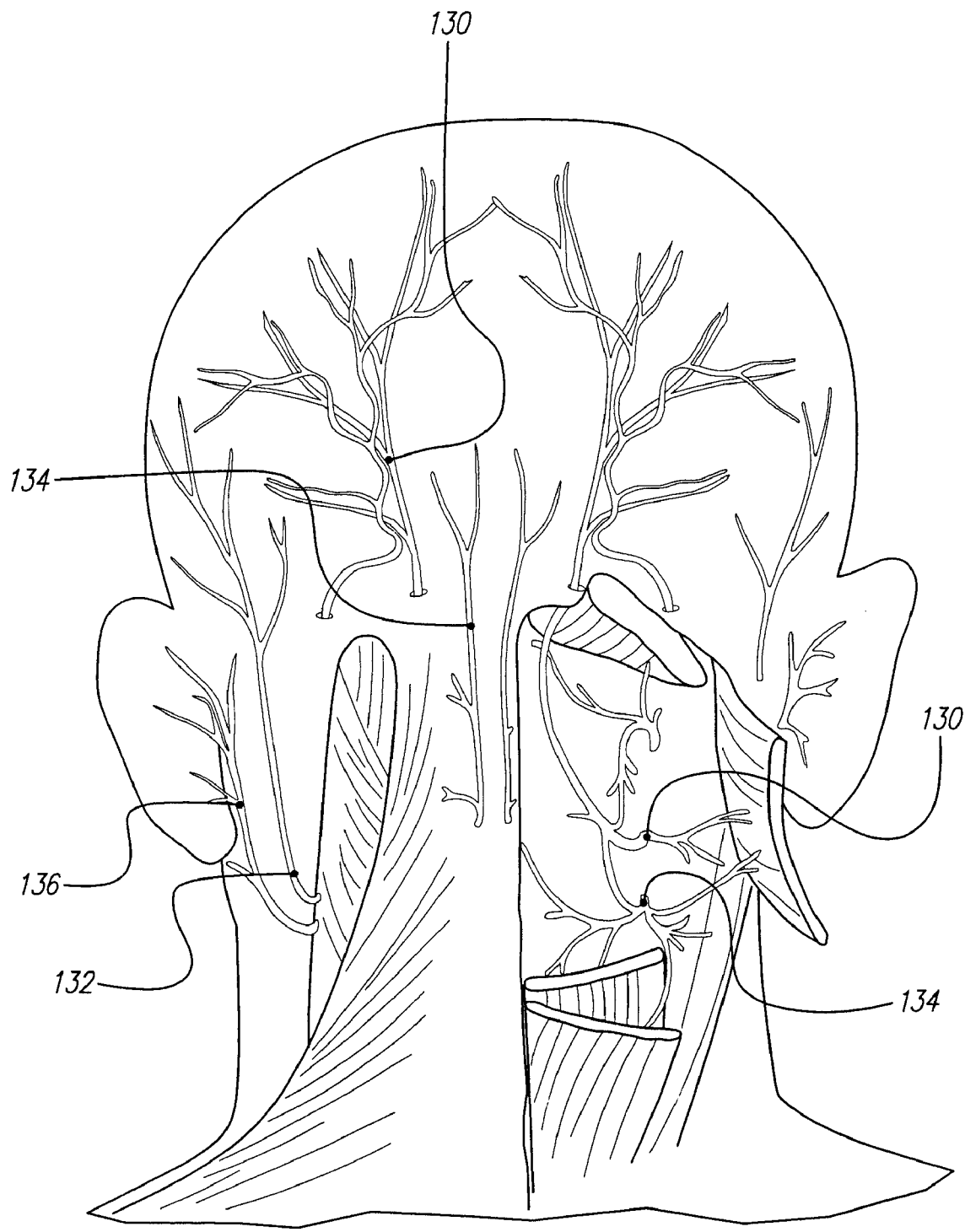
FIG. 2B depicts various nerves and muscles of the back of the head and neck.

FIGS. 1A and 1B depict the trigeminal nerve and its branches, while FIGS. 2A and 2B show nerves and muscles of the cervical plexus. The trigeminal nerve 100 on each side of the head arises from a trigeminal ganglion 102, which lies within the skull in an area known as Meckel's cave 110. In accordance with the teachings of the present invention, access to a trigeminal ganglion may be gained via the foramen ovale 112 or the foramen rotundum 114 in order to implant a miniature neurostimulator adjacent to one or both of the trigeminal ganglia 102.

Procedures that ablate the trigeminal ganglia 102 do not disable the muscles of mastication, since the cell bodies of the sensory portion of the nerve are within the trigeminal ganglion, whereas the motor portion simply projects axons through the ganglia (the motor neuron cell bodies are in the pons). This may provide a mechanism for selective stimulation of the sensory cells via appropriate placement of a microstimulator for stimulation of one or both trigeminal ganglia 102.

A miniature neurostimulator may additionally or alternatively be implanted adjacent to a trigeminal nerve 100 or any of its branches distal to the trigeminal ganglia 102, such as the ophthalmic nerve 120, the maxillary nerve 122, the mandibular nerve 124, and/or branch(es) of any of these. The ophthalmic nerve 120 exits the skull through the orbital fissure and provides sensation from the forehead. The maxillary nerve 122 exits the skull through the foramen rotundum 114 and provides sensation from the nose. The mandibular nerve 124 exits the skull through the foramen ovale 112 and provides sensation from the lips and jaw. The ophthalmic nerve 120 and the maxillary nerve 122 are entirely sensory, and sufficiently separate to allow independent and selective stimulation via appropriate placement of a microstimulator.

The mandibular nerve 124 is both sensory and motor. The mandibular nerve 124 innervates several facial muscles, including the muscles of mastication and the tensor tympani, which reflexively damps down the vibrations of the malleus by making the tympanic membrane more tense. However, just distal to the foramen ovale 112, the mandibular nerve 124 splits into a purely sensory branch that innervates the superior part of the lower jaw. And slightly more distally, another branch splits into a purely sensory branch that innervates the inferior part of the lower jaw. These branches may be sufficiently separate to allow independent and selective stimulation via appropriate placement of a microstimulator.

Headache and facial pain may also be relieved with stimulation additionally or alternatively applied to nerves arising from the upper cervical spine (C1–C4). As seen in FIGS. 2A and 2B, many of these nerves are relatively easily accessed, especially in their distal portions, since they lie subcutaneously in the back of the head or the back or sides of the neck. Examples of such nerves are the greater occipital nerve 130, the lesser occipital nerve 132, and the third occipital nerve 134, as well as the great auricular nerve(s) 136, a transverse cervical nerve(s) 138, a supraclavicular nerve(s) 140, and/or branches of any of these. In accordance with additional teachings of the present invention, stimulation of, for instance, one or more of these nerves is alternatively or additionally provided to relieve headache and/or facial pain.

In accordance with the teachings of the present invention, electrical stimulation at one or more of the above-mentioned and/or other cervical and/or trigeminal nerve branches is provided to relieve headache and/or facial pain. A microstimulator may be relatively easily implanted via injection and/or via endoscopic means adjacent to one or more of the above-identified nerves or nerve structures. A more complicated surgical procedure may be required for sufficient access to one or more of these nerve structures and/or for purposes of fixing the neurostimulator in place. The sites of injection or skin incision could be selected such that the scars would likely be covered by hair in most people.

Electrical stimulation of such neural structures may help attenuate or otherwise control the symptoms of headache and/or facial pain through direct neural stimulation via the "gate-control" mechanism, in which the activation of larger, non-nociceptive fibers compete with, or "gate", nociceptive signals. Under normal conditions, pain signals are carried from the source of the pain through afferent nerve fibers which convey the impulses toward a nerve center (e.g., the brain or spinal cord). These pain signals travel through relatively small diameter nerve fibers (i.e., A-$\delta$ and C fibers), which are also relatively slow-conducting fibers. Based on the gate control theory, stimulating the fast-conducting, larger diameter nerve fibers (i.e., A-$\alpha$ and/or A-$\beta$ fibers) will block, or gate, the slower pain signals from reaching the brain, or from being processed or recognized as pain signals. The somatic sensory fibers responsible for touch, pressure, and position sense are carried through these relatively large diameter nerve fibers. As such, relatively low amplitude stimulating current, which selectively activates these large diameter nerve fibers, may be applied to these nerve fibers to treat headaches and/or facial pain.

Through the interruption or disruption of the "trigeminovascular system", electrical stimulation may alternatively or additionally alter the rate of release of neuropeptides and/or other substances that mediate vasodilation and/or vasoconstriction, thus interrupting or otherwise altering the proinflammatory reaction (a.k.a. trigeminovascular neuroinflammatory cascade) thought to be involved in pain generation and transmission. Electrical stimulation may alternatively or additionally extinguish presumed foci of nociceptor discharges maintained by perivascular neurogenic inflammation, thereby reestablishing normal central neuron sensitivity and controlling or relieving headache, facial pain, and/or their symptoms.

As indicated above, the present invention is directed to treating headache and/or facial pain using one or more small, implantable neurostimulators, referred to herein as "microstimulators". The microstimulators of the present invention are preferably, but not necessarily, similar to or of the type referred to as BION™ devices. The following documents describe various features and details associated with the manufacture, operation, and use of BION implantable microstimulators, and are all incorporated herein by reference:

| Application/<br>Patent/<br>Publication No. | Filing/<br>Publication<br>Date | Title |
|---|---|---|
| U.S. Pat. No.<br>5,193,539 | Issued<br>Mar. 16, 1993 | Implantable Microstimulator |
| U.S. Pat. No.<br>5,193,540 | Issued<br>Mar. 16, 1993 | Structure and Method of Manufacture of an Implantable Microstimulator |
| U.S. Pat. No.<br>5,312,439 | Issued<br>May 17, 1994 | Implantable Device Having an Electrolytic Storage Electrode |
| U.S. Pat. No.<br>5,324,316 | Issued<br>June 28, 1994 | Implantable Microstimulator |
| U.S. Pat. No.<br>5,405,367 | Issued<br>Apr. 11, 1995 | Structure and Method of Manufacture of an Implantable Microstimulator |
| U.S. Pat. No.<br>6,051,017 | Issued<br>Apr. 18, 2000 | Improved Implantable Microstimulator and Systems Employing Same |
| PCT Publication<br>WO 98/37926 | published<br>Sept. 3, 1998 | Battery-Powered Patient Implantable Device |
| PCT Publication<br>WO 98/43700 | published<br>Oct. 8, 1998 | System of Implantable Devices For Monitoring and/or Affecting Body Parameters |
| PCT Publication<br>WO 98/43701 | published<br>Oct. 8, 1998 | System of Implantable Devices For Monitoring and/or Affecting Body Parameters |
| | published<br>September<br>1997 | Micromodular Implants to Provide Electrical Stimulation of Paralyzed Muscles and Limbs, by Cameron, et al., published in IEEE Transactions on Biomedical Engineering, Vol. 44, No. 9, pages 781–790. |

Figure 3:
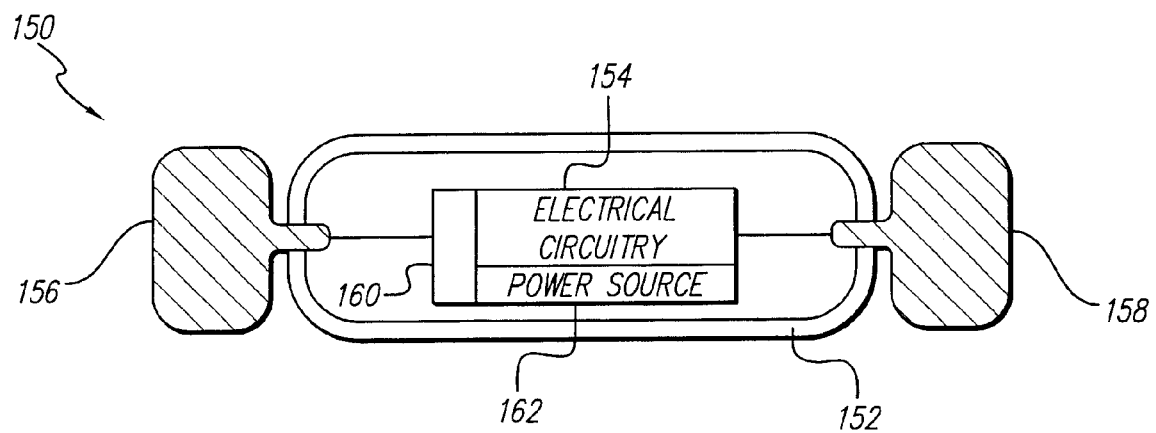
FIG. 3 illustrates an exemplary embodiment of a stimulation system of the present invention.

As shown in FIG. 3, microstimulator device 150 includes a narrow, elongated capsule 152 containing electronic circuitry 154 connected to electrodes 156 and 158, which may pass through the walls of the capsule at either end. As detailed in the referenced patent publications, electrodes 156 and 158 generally comprise a stimulating electrode (to be placed close to the nerve) and an indifferent electrode (for completing the circuit). Other configurations of microstimulator device 150 are possible, as is evident from the above-referenced patent publications, and as described in more detail herein.

Certain configurations of implantable microstimulator 150 are sufficiently small to permit its placement adjacent to the structures to be stimulated. (As used herein, "adjacent" and "near" mean as close as reasonably possible to targeted tissue, including touching or even being positioned within the tissue, but in general, may be as far as about 150 mm from the target tissue.) A single microstimulator 150 may be implanted, or two or more microstimulators may be implanted to achieve greater stimulation of the targeted tissue, or for a longer period of time.

Capsule 152 of FIG. 3 may have a diameter of about 4–5 mm, or only about 3 mm, or even less than about 3 mm. Capsule 152 length may be about 25–35 mm, or only about 20–25 mm, or even less than about 20 mm. The shape of the microstimulator may be determined by the structure of the desired target, the surrounding area, and the method of implantation. A thin, elongated cylinder with electrodes at the ends, as shown in FIG. 3, is one possible configuration, but other shapes, such as spheres, disks, or helical structures, are possible, as are additional electrodes.

Microstimulator 150 may be implanted with a surgical insertion tool specially designed for the purpose, or may be injected (e.g., via a hypodermic needle). Alternatively, device 150 may be implanted via conventional surgical methods, or may be inserted using other endoscopic or laparoscopic techniques. A more complicated surgical procedure may be required for fixing the neurostimulator in place.

The external surfaces of stimulator 150 may advantageously be composed of biocompatible materials. Capsule 152 may be made of, for instance, glass, ceramic, or other material that provides a hermetic package that will exclude water vapor but permit passage of electromagnetic fields used to transmit data and/or power. Electrodes 156 and 158 may be made of a noble or refractory metal or compound, such as platinum, iridium, tantalum, titanium, titanium nitride, niobium, or alloys of any of these, in order to avoid corrosion or electrolysis which could damage the surrounding tissues and the device.

In certain embodiments of the instant invention, microstimulator 150 comprises two, leadless electrodes. However, either or both electrodes 156 and 158 may alternatively be located at the ends of short, flexible leads as described in U.S. patent application Ser. 09/624,130, filed Jul. 24, 2000, which is incorporated herein by reference in its entirety. The use of such leads permits, among other things, electrical stimulation to be directed more locally to targeted tissue(s) a short distance from the surgical fixation of the bulk of the implantable stimulator 150, while allowing most elements of stimulator 150 to be located in a more surgically convenient site. This minimizes the distance traversed and the surgical planes crossed by the device and any lead(s). In most uses of this invention, the leads are no longer than about 150 mm.

Microstimulator 150 contains, when necessary and/or desired, electronic circuitry 154 for receiving data and/or power from outside the body by inductive, radio-frequency (RF), or other electromagnetic coupling. In some embodiments, electronic circuitry 154 includes an inductive coil for receiving and transmitting RF data and/or power, an integrated circuit (IC) chip for decoding and storing stimulation parameters and generating stimulation pulses (either intermittent or continuous), and additional discrete electronic components required to complete the electronic circuit functions, e.g. capacitor(s), resistor(s), coil(s), and the like.

Neurostimulator 150 includes, when necessary and/or desired, a programmable memory 160 for storing a set(s) of data, stimulation, and control parameters. Among other things, memory 160 may allow stimulation and control parameters to be adjusted to settings that are safe and efficacious with minimal discomfort for each individual. Specific parameters may provide therapeutic advantages for various forms of headache and/or facial pain. For instance, some patients may respond favorably to intermittent stimulation, while others may require continuous stimulation to alleviate their pain.

In addition, stimulation parameters may be chosen to target specific neural populations and to exclude others, or to increase neural activity in specific naural populations and to decrease neural activity in others. For example, relatively low frequency neurostimulation (i.e., less than about 100–150 Hz) typically has an excitatory effect on surrounding neural tissue, leading to increased neural activity, whereas relatively high frequency neurostimulation (i.e., greater than about 100–150 Hz) may have an inhibitory effect, leading to decreased neural activity. In addition, large diameter nerve fibers (e.g., A-α and/or A-β fibers) respond to relatively low amplitude electrical current pulses compared with small diameter fibers (e.g., A-δ and/or C fibers). As mentioned earlier, nociceptive fibers are typically small diameter C-fibers.

Some embodiments of implantable stimulator 150 also includes a power source and/or power storage device 162. Possible power options for a stimulation device of the present invention, described in more detail below, include but are not limited to an external power source coupled to stimulator 150, e.g., via an RF link, a self-contained power source utilizing any suitable means of generation or storage of energy (e.g., a primary battery, a replenishable or rechargeable battery such as a lithium ion battery, an electrolytic capacitor, a super- or ultra-capacitor, or the like), and if the self-contained power source is replenishable or rechargeable, means of replenishing or recharging the power source (e.g., an RF link, an optical link, a thermal link, or other energy-coupling link).

According to certain embodiments of the invention, a microstimulator operates independently. According to various embodiments of the invention, a microstimulator operates in a coordinated manner with other microstimulator(s), other implanted device(s), or other device(s) external to the patient's body. For instance, a microstimulator may control or operate under the control of another implanted microstimulator(s), other implanted device(s), or other device(s) external to the patient's body. A microstimulator may communicate with other implanted microstimulators, other implanted devices, and/or devices external to a patient's body via, e.g., an RF link, an ultrasonic link, a thermal link, an optical link, or the like. Specifically, a microstimulator may communicate with an external remote control (e.g., patient and/or physician programmer) that is capable of sending commands and/or data to a microstimulator and that may also be capable of receiving commands and/or data from a microstimulator.

Figure 4:
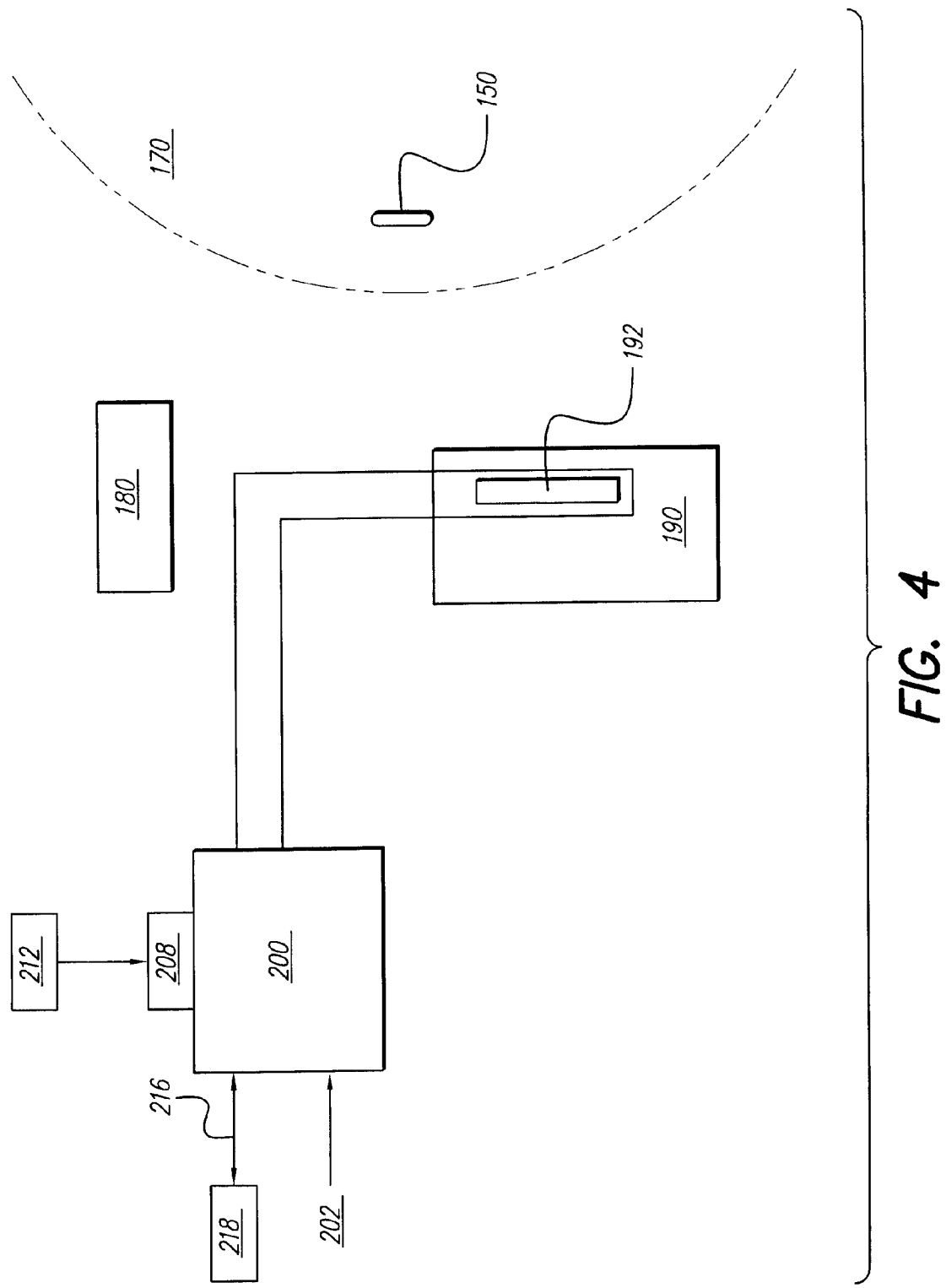
FIG. 4 illustrates exemplary external components of the invention.

In certain embodiments, and as illustrated in FIG. 4, the patient 170 switches the implantable stimulator 150 on and off by use of controller 180, which may be handheld. Implantable stimulator 150 is operated by controller 180 by any of various means, including sensing the proximity of a permanent magnet located in controller 180, sensing RF transmissions from controller 180, or the like.

External components for programming and/or providing power to various embodiments of implantable stimulator 150 are also illustrated in FIG. 4. When communication with the implanted stimulator 150 is desired, patient 170 is positioned on or near external appliance 190, which appliance contains one or more inductive coils 192 or other means of communication (e.g., RF transmitter and receiver). External appliance 190 is connected to or is a part of external electronic circuitry appliance 200 which may receive power 202 from a conventional power source. External appliance 200 contains manual input means 208, e.g., a keypad, whereby the patient 170 or a caregiver 212 can request changes in the stimulation parameters produced during the normal operation of the implantable stimulator 150. In these embodiments, manual input means 208 includes various electromechanical switches and/or visual display devices that provide the patient and/or caregiver with information about the status and prior programming of the implantable stimulator 150.

Alternatively or additionally, external electronic appliance 200 is provided with an electronic interface means 216 for interacting with other computing means 218, such as by a serial interface cable or infrared link to a personal computer or to a telephone modem or the like. Such interface means 216 may permit a clinician to monitor the status of the implant and prescribe new stimulation parameters from a remote location.

The external appliance(s) may be embedded in a cushion, pillow, hat, or garment. Other possibilities exist, including a headband, patch or other structure(s) that may be affixed to the patient's body or clothing. External appliances may include a package that can be, e.g., worn on the belt, may include an extension to a transmission coil affixed, e.g., with a velcro band or adhesive, or may be combinations of these or other structures able to perform the functions described herein.

In order to help determine the strength and/or duration of electrical stimulation required to produce the desired effect, in some embodiments, a patient's response to and/or need for treatment is sensed. For example, electrical activity of a nerve (e.g., ENG), electrical activity of the brain (e.g., EEG), muscle activity (e.g., EMG), and/or patient mobility (e.g., cumulative accelerometer activity) may be sensed. Other measures of the state of the patient may additionally or alternatively be sensed. For instance, medication, neurotransmitter, hormone, cytokine, neuropeptide, endorphin, and/or enzyme levels or their changes, and/or levels or changes in other substance(s) borne in the blood and/or in the cerebrospinal fluid (CSF) may be sensed, using, e.g., one or more Chemically Sensitive Field-Effect Transistors (CHEMFETs) such as Enzyme-Selective Field-Effect Transistors (ENFETs) or Ion-Sensitive Field-Effect Transistors (ISFETs, as are available from Sentron CMT of Enschede, The Netherlands).

For example, when electrodes of implantable stimulator 150 are implanted adjacent to a trigeminal nerve branch, a sensor or stimulating electrode (or other electrode) of microstimulator 150 may be used to sense changes in ENG resulting from the stimulation applied to the nerve. Alternatively, a "microstimulator" dedicated to sensory processes communicates with a microstimulator that provides the stimulation pulses. The implant circuitry 154 may, if necessary, amplify and transmit these sensed signals, which may be analog or digital. Other methods of determining the required stimulation include a sensor on one or more of the sympathetic ganglia for sensing increased sympathetic discharge and other markers of the potential for pain, a sensor implanted in the brain in an area where altered activity correlates with possible pain (e.g., the sensory thalamus), as well as other methods mentioned herein, and yet others that will be evident to those of skill in the art upon review of the present disclosure. The sensed information may be used to control stimulation parameters in a closed-loop manner.

For instance, in several embodiments of the present invention, a first and second "stimulator" are provided. The second "stimulator" periodically (e.g. once per minute) records a level of neural activity (or endorphin level, or cumulative accelerometer activity, etc.), which it transmits to the first stimulator. The first stimulator uses the sensed information to adjust stimulation parameters according to an algorithm programmed, e.g., by a physician. For example, the amplitude of stimulation may be increased in response to increased activity in nerves, nerve fibers, or brain areas which demonstrate increased activity during pain. In some alternatives, one stimulator performs both the sensing and stimulating functions, as discussed in more detail presently.

While a microstimulator may also incorporate means of sensing pain, it may alternatively or additionally be desirable to use a separate or specialized implantable device to record and telemeter physiological conditions/responses in order to adjust stimulation parameters. This information may be transmitted to an external device, such as external appliance 190, or may be transmitted directly to implanted stimulator(s) 150. However, in some cases, it may not be necessary or desired to include a sensing function or device, in which case stimulation parameters are determined and refined, for instance, by patient feedback, or the like.

Thus, it is seen that in accordance with the present invention, one or more external appliances may be provided to interact with microstimulator 150, and may be used to accomplish, potentially among other things, one or more of the following functions:

Function 1: If necessary, transmit electrical power from the external electronic appliance 200 via appliance 190 to the implantable stimulator 150 in order to power the device and/or recharge the power source/storage device 162. External electronic appliance 200 may include an automatic algorithm that adjusts stimulation parameters automatically whenever the implantable stimulator(s) 150 is/are recharged.

Function 2: Transmit data from the external appliance 200 via the external appliance 190 to the implantable stimulator 150 in order to change the operational parameters (e.g., electrical stimulation parameters) used by stimulator 150.

Function 3: Transmit sensed data indicating a need for treatment or in response to stimulation from implantable stimulator 150 (e.g., ENG, EEG, change in neurotransmitter level, or other activity) to external appliance 200 via external appliance 190.

Function 4: Transmit data indicating state of the implantable stimulator 150 (e.g., battery level, stimulation settings, etc.) to external appliance 200 via external appliance 190.

By way of example, a treatment modality for migraine headache may be carried out according to the following sequence of procedures:

1. A stimulator 150 is implanted so that its electrodes 156 and 158 are adjacent to a trigeminal ganglion 102. If necessary or desired, one or more additional stimulator(s) 150 may additionally or alternatively be implanted adjacent to other nerve structures, such as the trigeminal nerve 100, the ophthalmic nerve 120, the maxillary nerve 122, the mandibular nerve 124, any of the occipital nerves, any other nerves arising from the upper cervical spine, and/or branches of any of these nerves.

2. Using Function 2 described above (i.e., transmitting data) of external electronic appliance 200 and external appliance 190, stimulator 150 is commanded to produce a series of electrical stimulation pulses with gradually increasing amplitude.

3. After each stimulation pulse, series of pulses, or at some other predefined interval, any change in, e.g., ENG and/or neurotransmitter level is sensed, for instance, by one or more electrodes 156 and 158 or sensors (e.g., a CHEMFET). These responses are converted to data and telemetered out to external electronic appliance 200 via Function 3.

4. From the response data received at external appliance 200 from the implantable stimulator 150, or from other assessment, the stimulus threshold for obtaining a response is determined and is used by a clinician acting directly 212 or by other computing means 218 to transmit the desired stimulation parameters to the implantable stimulator 150 in accordance with Function 2.

5. When patient 170 desires to invoke electrical stimulation to alleviate symptoms, patient 170 employs controller 180 to set the implantable stimulator 150 in a state where it delivers a prescribed stimulation pattern from a predetermined range of allowable stimulation patterns.

6. To cease electrical stimulation, patient 170 employs controller 180 to turn off stimulator 150.

7. Periodically, the patient or caregiver recharges the power source/storage device 162 of implantable stimulator 150, if necessary, in accordance with Function 1 described above (i.e., transmit electrical power).

For the treatment of any of the various types and degrees of headache and/or facial pain, it may be desirable to modify or adjust the algorithmic functions performed by the implanted and/or external components, as well as the surgical approaches, in ways that would be obvious to skilled practitioners of these arts. For example, in some situations, it may be desirable to employ more than one implantable stimulator 150, each of which could be separately controlled by means of a digital address. Multiple channels and/or multiple patterns of stimulation might thereby be programmed by the clinician and controlled by the patient in order to, for instance, deal with bilateral or complex headache.

In some embodiments discussed earlier, microstimulator 150, or a group of two or more microstimulators, is controlled via closed-loop operation. A need for and/or response to stimulation is sensed via microstimulator 150, or by an additional microstimulator (which may or may not be dedicated to the sensing function), or by another implanted or external device. If necessary, the sensed information is transmitted to microstimulator 150. In some embodiments, the stimulation parameters used by microstimulator 150 are automatically adjusted based on the sensed information. Thus, the stimulation parameters are adjusted in a closed-loop manner to provide stimulation tailored to the need for and/or response to stimulation.

For instance, in some embodiments of the present invention, a first and second "stimulator" are provided. The second "stimulator" periodically (e.g. once per minute) records a level of e.g., corticosteroids, catecholamines or their breakdown products, and/or medication level (for instance, of an opiate or a triptan drug), which it transmits to the first stimulator. Serum levels of corticosteroids and/or catecholamines may be increased during times of stress or anxiety and may thus be increased at the onset of headache and/or facial pain, or upon an increase in the intensity of headache and/or facial pain. The first stimulator uses the sensed information to adjust stimulation parameters according to an algorithm programmed, e.g., by a clinician. For example, electrical stimulation amplitude may be activated or increased in response to increased levels of corticosteroids, catecholamines or their breakdown products, and/or medication level. Alternatively, one "microstimulator" performs both the sensing and stimulating functions.

Figure 5:
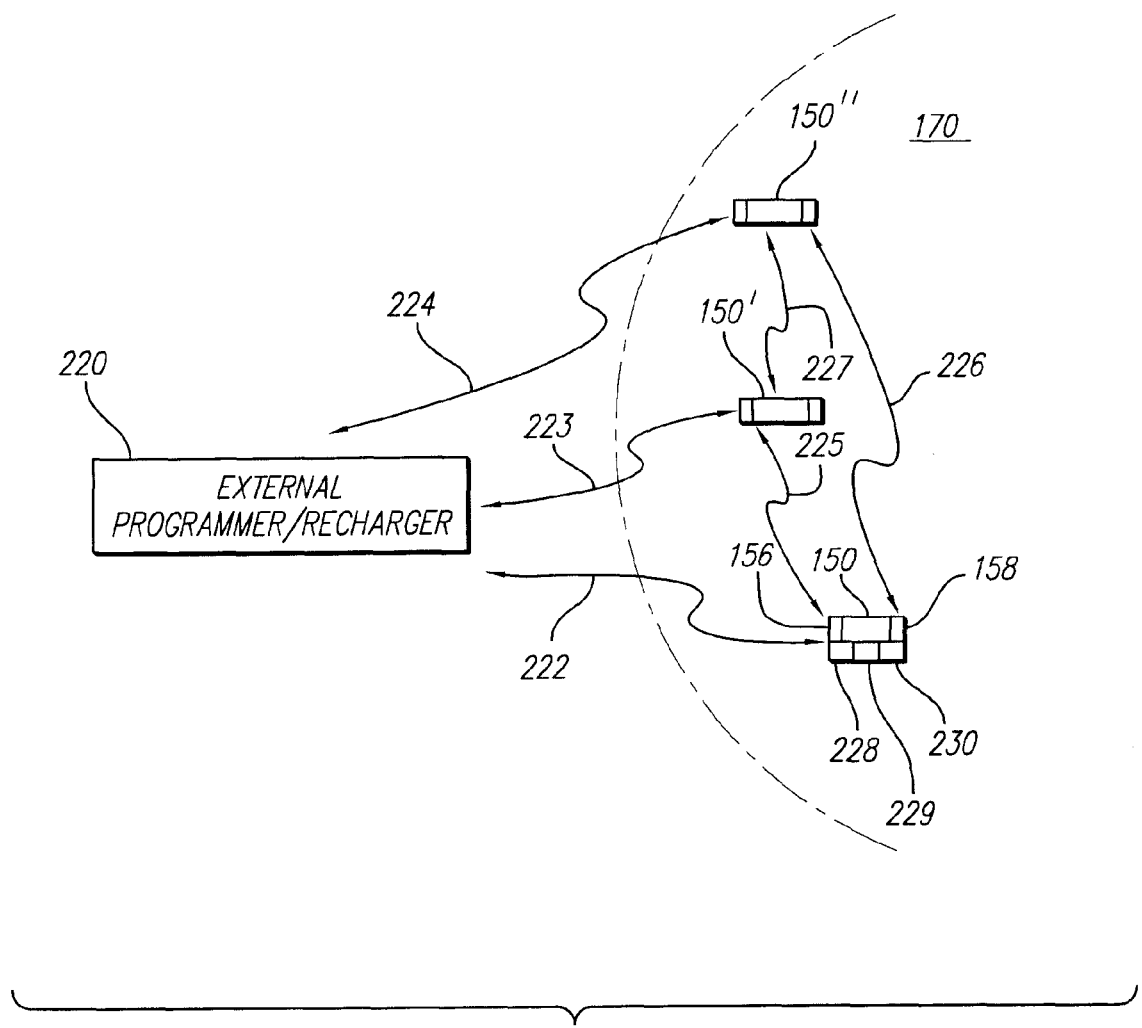
FIG. 5 depicts a system of implantable devices that communicate with each other and/or with external control/programming devices.

For example, as shown in the example of FIG. 5, a first microstimulator 150, implanted beneath the skin of patient 170, provides electrical stimulation via electrodes 156 and 158 to a first location; a second microstimulator 150' provides electrical stimulation to a second location; and a third microstimulator 150" provides electrical stimulation to a third location. As mentioned earlier, the implanted devices may operate independently or may operate in a coordinated manner with other similar implanted devices, other implanted devices, or other devices external to the patient's body, as shown by the control lines 222, 223 and 224 in FIG. 5. That is, in accordance with certain embodiments of the invention, external controller 220 controls the operation of each of the implanted microstimulators 150, 150' and 150".

According to various embodiments of the invention, an implanted device, e.g. microstimulator 150, may control or operate under the control of another implanted device(s), e.g., microstimulator 150' and/or microstimulator 150". That is, a device made in accordance with the invention may communicate with other implanted stimulators, other implanted devices, and/or devices external to a patient's body, e.g., via an RF link, an ultrasonic link, a thermal link, an optical link, or other communications link. Specifically, as illustrated in FIG. 5, microstimulator 150, 150', and/or 150", made in accordance with the invention, may communicate with an external remote control (e.g., patient and/or physician programmer 220) that is capable of sending commands and/or data to implanted devices and that may also be capable of receiving commands and/or data from implanted devices.

A microstimulator made in accordance with the invention may incorporate, in some embodiments, first sensing means 228 for sensing therapeutic effects, clinical variables, or other indicators of the state of the patient, such as ENG, EEG, EMG, patient mobility, sympathetic discharge, and/or other marker of the potential for pain. The stimulator additionally or alternatively incorporates second means 229 for sensing levels or changes in one or more medications, neurotransmitters, cytokines, hormones, neuropeptides, endorphins, enzymes, and/or other substances in the blood plasma, in the cerebrospinal fluid, or in the local interstitial fluid. The stimulator additionally or alternatively incorporates third means 230 for sensing electrical current levels and/or waveforms supplied by another source of electrical energy. Sensed information may be used to control the parameters of the stimulator(s) in a closed loop manner, as shown by control lines 225, 226, and 227. Thus, the sensing means may be incorporated into a device that also includes electrical stimulation means, or the sensing means (that may or may not have stimulating means) may communicate the sensed information to another device(s) with stimulating means.

While a microstimulator may also incorporate means of sensing the condition of a patient, e.g., via ENG, EEG, EMG, or patient mobility, it may alternatively or additionally be desirable to use a separate or specialized implantable device to sense and telemeter physiological conditions/ responses in order to adjust stimulation parameters. This information may be transmitted to an external device, such as external appliance 220, or may be transmitted directly to implanted stimulator(s) 150. However, in some cases, it may not be necessary or desired to include a sensing function or device, in which case stimulation parameters may be determined and refined, for instance, by patient feedback.

As mentioned earlier, large diameter fibers (e.g., A-α and A-β fibers) respond to relatively lower current density stimulation vis-a-vis small diameter fibers (e.g., A-δ and C fibers). These smaller A-δ and C fibers are generally responsible for carrying pain and temperature signals, while the A-α and A-β fibers generally carry pressure, light touch, and proprioceptive information. Therefore, pain may be masked, decreased or otherwise controlled or removed by activating the larger A-α and/or A-β fibers, so the signals from the A-δ and/or C fibers are "masked," or "gated."

For example, microstimulator(s) 150 may be implanted adjacent to one or more trigeminal nerve branches or structures and/or nerve branches arising from the upper cervical spine. In some embodiments of the invention, the microstimulator(s) are programmed to provide relatively low-amplitude current stimulation pulses (e.g., at less than about 1–10 mA, depending on proximity of the stimulator to the target neural tissue), which is likely to cause the sensation of pressure, light touch, proprioceptive, and other non-nociceptive sensations. These sensations may be sufficient to mask, block, or otherwise attenuate or control the pain signals.

According to several embodiments of the invention, pain is alleviated by additionally or alternatively increasing excitement of these nerve fibers. Relatively low-frequency electrical stimulation (e.g., less than about 100–150 Hz) is likely to produce such excitement. This low-frequency therapy is most likely to provide relief to patients with some types of headache and/or facial pain.

According to various embodiments of the invention, pain is alleviated by additionally or alternatively decreasing excitement of these nerve fibers. Relatively high-frequency electrical stimulation (e.g., greater than about 100–150 Hz) is likely to produce such inhibition. This therapy is most likely to provide relief to patients with some other types of headache and/or facial pain.

Additionally, sensing means described earlier may be used to orchestrate first the activation of microstimulator(s) targeting one or more nerves to control pain in one area, and then, when appropriate, the microstimulator(s) targeting nerves that control pain in another area and/or by a different means. Alternatively, this orchestration may be programmed, and not based on a sensed condition.

While the invention herein disclosed has been described by means of specific embodiments and applications thereof, numerous modifications and variations could be made thereto by those skilled in the art without departing from the scope of the invention set forth in the claims.

What is claimed is:

1. A method for treating a patient with headache and/or facial pain, comprising:
   providing at least one leadless stimulator having at least two electrodes;
   implanting the at least one stimulator adjacent to at least one nerve structure at least in part responsible for sensations in a region experiencing headache and/or facial pain;
   providing operating power to the at least one stimulator;
   using at least one external appliance to transmit stimulation parameters to the at least one stimulator;
   receiving and storing the stimulation parameters;
   generating stimulation pulses in accordance with the stimulation parameters; and
   delivering the stimulation pulses to nerves adjacent to the at least one stimulator;
   wherein the stimulator has a size and shape suitable for placement of the electrodes adjacent to the at least one nerve structure.

2. The method of claim 1 wherein the stimulation pulses are delivered at less than about 1–10 mA.

3. The method of claim 1 wherein the at least one nerve structure comprises at least one of a trigeminal nerve, a branch of the trigeminal nerve, a trigeminal ganglion, an ophthalmic nerve, a branch of the ophthalmic nerve, a maxillary nerve, a branch of the maxillary nerve, a mandibular nerve, a branch of the mandibular nerve, a greater occipital nerve, a branch of the greater occipital nerve, a lesser occipital nerve, a branch of the lesser occipital nerve, a third occipital nerve, a branch of the third occipital nerve, a great auricular nerve, a branch of the great auricular nerve, a transverse cervical nerve, a branch of the transverse cervical nerve, a supraclavicular nerve, and a branch of the supraclavicular nerve.

4. The method of claim 3 wherein the stimulation pulses are delivered at less than about 1–10 mA.

5. The method of claim 3 wherein the stimulation pulses are delivered at less than about 100 to 150 Hz.

6. The method of claim 3 wherein the stimulation pulses are delivered at greater than about 100 to 150 Hz.

7. The method of claim 1 further comprising providing at least one sensor;

using the at least one sensor to sense a physical condition; and determining the stimulation parameters based upon the sensed condition.

8. The method of claim 7 wherein the at least one sensor is a part of the stimulator.

9. The method of claim 7 wherein the stimulation pulses are delivered at less than about 1–10 mA.

10. The method of claim 1 further comprising providing and implanting more than one stimulator.

11. A method for treating a patient with headache and/or facial pain comprising:

providing at least one leadless stimulator having at least two electrodes;

providing at least one sensor;

implanting the at least one stimulator adjacent to at least one nerve structure at least in part responsible for sensation in a region experiencing headache and/or facial pain;

providing operating power to the at least one stimulator;

using the sensor to sense a physical condition;

determining stimulation parameters based upon the sensed condition;

generating stimulation pulses in accordance with the stimulation parameters; and delivering the stimulation pulses to nerve structures adjacent to the at least two electrodes;

wherein the stimulator has a size and shape suitable for placement of the electrodes adjacent to the at least one nerve structure.

12. The method of claim 11 wherein the at least one sensor is a part of the stimulator.

13. The method of claim 11 wherein the stimulation parameters are determined using at least one external appliance.

14. The method of claim 11 wherein providing power to the at least one stimulator comprises receiving power from at least one external appliance.

15. The method of claim 14 wherein providing power to the at least one stimulator further comprises storing the power received from the at least one external appliance.

16. The method of claim 11 further comprising providing and implanting more than one stimulator.

17. The method of claim 11 wherein the at least one nerve structure comprises at least one of a trigeminal nerve, a branch of the trigeminal nerve, a trigeminal ganglion, an ophthalmic nerve, a branch of the ophthalmic nerve, a maxillary nerve, a branch of the maxillary nerve, a mandibular nerve, a branch of the mandibular nerve, a greater occipital nerve, a branch of the greater occipital nerve, a lesser occipital nerve, a branch of the lesser occipital nerve, a third occipital nerve, a branch of the third occipital nerve, a great auricular nerve, a branch of the great auricular nerve, a transverse cervical nerve, a branch of the transverse cervical nerve, a supraclavicular nerve, and a branch of the supraclavicular nerve.

18. The method of claim 11 wherein the sensor senses at least one of electrical activity of a nerve, electrical activity of the brain, muscle activity, and patient mobility.

19. The method of claim 11 wherein the sensor senses at least one of sympathetic discharge, medication level, neurotransmitter level, hormone level, cytokine level, neuropeptide level, endorphin level, enzyme level, and level of a bloodborne substance.

* * * * *